(12) United States Patent
Niazi

(10) Patent No.: US 6,251,421 B1
(45) Date of Patent: Jun. 26, 2001

(54) PHARMACEUTICAL COMPOSITION CONTAINING PSYLLIUM FIBER AND A LIPASE INHIBITOR

(76) Inventor: Sarfaraz K. Niazi, 20 Riverside Dr., Deerfield, IL (US) 60015

( * ) Notice: Subject to any disclaimer, the term of this patent is extended or adjusted under 35 U.S.C. 154(b) by 0 days.

(21) Appl. No.: 09/669,500

(22) Filed: Sep. 25, 2000

(51) Int. Cl.[7] .............................. A61K 9/20; A61K 9/48; A61K 9/14; A61K 9/46; A61K 9/50
(52) U.S. Cl. ..................... 424/441; 424/464; 424/451; 424/484; 424/486; 424/489; 424/466; 424/501; 424/738; 514/772.4
(58) Field of Search ..................... 424/464, 451, 424/486, 484, 489, 497, 466, 441, 501, 738; 514/772.4

(56) References Cited

U.S. PATENT DOCUMENTS 5,540,917 * 7/1996 Isler et al. ..................... 424/78.01
6,030,953 * 2/2000 Bailly et al. ..................... 514/24

FOREIGN PATENT DOCUMENTS

01090131 * 4/1989 (JP) .

* cited by examiner

Primary Examiner—Thurman K. Page
Assistant Examiner—Rachel M. Bennett
(74) Attorney, Agent, or Firm—Welsh & Katz, Ltd.

(57) ABSTRACT

The present invention provides orally administrable pharmaceutical compositions containing an inhibitor of gastrointestinal lipase, and at least one compound selected from the group consisting of psyllium husk, its seeds and leaves thereof. Methods are provided for preventing and treating anal leakage of oil in a patient to whom a composition containing an inhibitor of gastrointestinal lipase is orally administered.

13 Claims, No Drawings

PHARMACEUTICAL COMPOSITION CONTAINING PSYLLIUM FIBER AND A LIPASE INHIBITOR

BACKGROUND OF THE INVENTION

The present invention relates to pharmaceutical compositions containing an inhibitor of gastrointestinal lipase, and at least one compound selected from the group consisting of psyllium husk, its derivatives and salts thereof.

Psyllium husk, has a long history of use in traditional and herbal medicine and has been in use in the United States over 60 years ago. Psyllium husk is derived from the seed or leaves of the *Plantago ovata* plant. Besides *Plantago ovata*, psyllium is also known as Ispaghula and Ispagol. *Plantago ovata* is an annual herb native to Asia, the Mediterranean region, and North Africa. Psyllium grows in sand and silty soils. Currently, psyllium is extensively cultivated in India and Pakistan. India provides about 85% of the psyllium available in the world market. The US is the world's largest importer of psyllium husk. Psyllium has a long history of use through the world and has been used in traditional medicine in the United States, Europe, India, and China. Some of the uses of psyllium in traditional medicine are as laxative, emollient, demulcent, and diuretic.

Currently in the United States, psyllium husk is most often used as a bulk fiber laxative, in foods or in various fiber supplements. In 1998, the Food and Drug Administration (FDA) authorized the use in a health claim in the labeling of foods and dietary supplements containing psyllium husk. The health claim may state that diets low in saturated fat and cholesterol that include 7 grams of soluble fiber per day from psyllium may reduce the risk of heart disease by lowering cholesterol levels in the blood.

Psyllium is a bulk forming fiber. Other fibers that belong to the class of bulk forming fibers are cellulose, methylcellulose, sodium carboxymethylcellulose, karaya, malt soup extract, polycarbophil, and wheat bran. Bulk forming fibers are laxatives because of their water holding properties. They exert their action primarily through mechanical effects by bulking the colonic contents and shortening transit time.

Anal leakage of oil (oily spotting) is an adverse effect which is occasionally observed in patients treated with lipase inhibitors. It results from physical separation of some liquid unabsorbed dietary fat from the bulk of the fecal mass in the lower large intestine.

SUMMARY OF THE INVENTION

It has now been found that by combining a lipase inhibitor with effective amounts of psyllium, psyllium husk or the seeds or leaves thereof, the phenomenon of anal leakage of oil can be strongly reduced. The present invention is directed to pharmaceutical compositions containing an effective amount of an inhibitor of gastrointestinal lipase, and an effective amount of at least one compound selected from the group consisting of psyllium fiber or husk, its derivatives and salts thereof. The compositions of the present invention also optionally include auxiliary excipients.

The present invention is also concerned with the use of psyllium, psyllium husk or the seeds or leaves thereof for the combined simultaneous, separate or chronologically spaced use with an inhibitor of gastrointestinal lipase, such as orlistat or Pluronic L101, in the treatment of obesity and hyperlipaemia and their comorbidities, such as type II diabetes mellitus.

Artificial non-absorbed fats, mostly sucrose polyester, are used in the food industry for the production of low fat foods, such as low fat potato chips, low fat cookies, low fat salad dressings and low fat ice cream. The ingestion of higher amounts of such foodstuffs containing non-absorbable fats can induce oily leakage.

The pharmaceutical compositions of the present invention reduce fat absorption through inhibition of gastrointestinal lipase. The invention is further concerned with the use of psyllium, psyllium husk or the seeds or leaves thereof for treating or preventing the syndrome of anal leakage of oil occurring after the administration of an inhibitor of gastrointestinal lipase, such as orlistat or Pluronic L101, or after ingestion of food containing poorly absorbable or non-absorbable fats or oils or of undigestible oily fat substitutes.

Methods are provided for treating or preventing the syndrome of anal leakage of oil in a patient to whom a composition containing an inhibitor of gastrointestinal lipase is orally administered in unit dosage form.

DETAILED DESCRIPTION OF THE INVENTION

Examples of lipase inhibitors which can be used in the compositions of the present invention are orlistat or Pluronic L101, lipstatin, panclicins, hesperidin, ebelactones, esterastin and their derivatives, and valilactone or such natural compounds as *Cassia Nomame*. The most preferred lipase inhibitor is orlistat or Pluronic L101.

Orlistat reduces the absorption of dietary fat. Its use for the control or prevention of obesity and hyperlipaemia, is described in U.S. Pat. No. 4,598,089. Orlistat is an N-formyl-L-leucine ester with (3S,4S)-3-hexyl-4-[(2S)-2-hydroxytridecyl]-2-oxetanone. Its chemical structure is as follows:

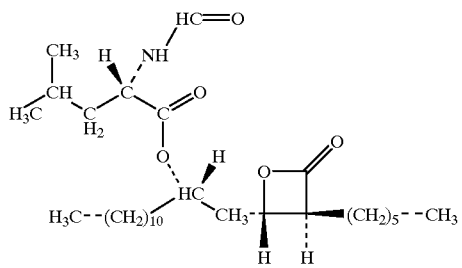

Another example of gastrointestinal lipase inhibitor is Pluronic L101 which is a hydrophobic surface-active agent, and potent in-vitro inhibitor of human pancreatic lipase. When administered as a 1 percent or 3 percent dietary admix to meal-fed rats, pluronic L-101 produced a significant and dose-dependent decrease in body weight gain while not affecting food consumption. Excretion of dietary fat in the feces was enhanced significantly in a dose-dependent manner during Pluronic L-101 treatment.

Pluronic is a poloxamer, a nononionic surfactant, and a block copolymer of propyleneoxide and ethylene oxide. The propylene oxide block is sandwiched between two ethylene oxide blocks, as follows:

where x,z=2-128 y=16-67

In Pluronic L101, x, z=7; y=54

Any conventional auxiliary excipients can be used in formulating the dosage forms of the present invention.

Examples of auxiliary excipients which can be used in the pharmaceutical compositions of the invention are binders, dilutens and lubricants, such as AVICEL, polyvinyl pyrrolidone (povidone), talc and sodium stearyl fumarate; sweeteners, such as sorbitol, glucose, saccharose, saccharine-sodium salt and sodium cyclamate; flavor agents, such as passion fruit, citron and limette; flavor enhancers, such as citric acid, monosodium citrate, sodium chloride and chinine sulfate; effervescing agents, such as sodium bicarbonate and tartaric acid, disintegrants, antimicrobial agents, such as p-hydroxybenzoic acid methyl or propyl ester; detergents and coloring agents, such as beta-carotene.

The experiment for loss of free fecal oil is based on the observation that mice, due to steadily grooming their furs, distribute any excreted free fecal oil all over their bodies. This results in an easily visible brownish coloring of the fur (oily fur greasing). In mice weighing 20–25 g, excretion of free oil is provoked by administering an excessive dose of orlistat or Pluronic L101 (300 .mu.mol/kg/day) together with a diet containing 7% fat, resulting in a daily fat intake of 1 g/day. The diet consists of mashed Hamburger, butter, French fries and string beans. When the diet contained psyllium, the extent of oily fur greasing is reduced, when compared to controls.

The compositions of the present invention reduce fat absorption in a patient through the use of a gastrointestinal lipase inhibitor to inhibit gastrointestinal lipase. The compositions also treat and prevent the syndrome of anal leakage of oil that can occur in a patient upon administration of the gastrointestinal lipase inhibitor. The compositions of the invention contain from 10 to 50, preferably from 20 to 40, parts by weight of psyllium, psyllium husk, seeds or leaves from 10 to 200, preferably from 20 to 80, parts by weight of auxiliary excipients for 1 part by weight of an inhibitor of gastrointestinal lipase, such as orlistat or Pluronic L101. The inhibitor of gastrointestinal lipase in the compositions of the invention is present in an amount at least sufficient to reduce the absorption of fat in the meal consumed by a patient.

The composition of the invention can also be in the form of a commercial pack containing an inhibitor of gastrointestinal lipase and psyllium, psyllium husk or the seeds or leaves thereof, with instructions for its use for the simultaneous, separate or chronologically spaced use in the treatment of obesity or hyperlipaemia.

For the treatment or prevention of obesity or hyperlipaemia, a composition of the invention containing from 10 mg to 1 g of an inhibitor of gastrointestinal lipase, such as orlistat, and from 15 g to 20 g, preferably from 2 g to 10 g, of psyllium, psyllium husk or the seeds or leaves thereof, can be administered orally once, twice or three times per day.

The compositions of the invention can be administered to patients in oral dosage forms. For example, the compositions can be administered as drinkable formulations, such as solutions or suspensions prepared from powder, granules, pellets, tablets to be reconstituted or effervescent tablets; or in form of chewable formulations, such as tablets, capsules or lozenges. They can also be incorporated into food preparations, such as wafers, crackers or bread, or can be in form of swallowable formulations, such as tablets or capsules.

A preferred composition of the invention is a tablet for the treatment of obesity, consisting essentially of orlistat or Pluronic L101 as the active ingredient and psyllium husk, wherein the dosage is from 10 to 120 mg of orlistat or Pluronic L101 and from 0.5 to 5 g of psyllium husk. Most preferably, the tablet consists essentially of about 60 mg of orlistat or Pluronic L101 and about 2.5 g of psyllium husk. Preferably, the tablet is chewable.

A further preferred composition of the invention is a wafer for the treatment of obesity, consisting essentially of orlistat or Pluronic L101 as the active ingredient and psyllium husk, wherein the dosage is from 10 to 200 mg of orlistat or Pluronic L101 and from 1 to 10 g of psyllium husk. Most preferably, the wafer consists essentially of about 120 mg of orlistat or Pluronic L-101 and about 5 g of psyllium husk.

In accordance with the present invention, methods are provided for treating or preventing the syndrome of anal leakage of oil in a patient to whom a composition containing an inhibitor of gastrointestinal lipase is being orally administered in unit dosage form. Treating or preventing the syndrome of anal leakage of oil in a patient is accomplished by orally administering to a patient per meal consumed by the patient a composition in unit dosage form containing an inhibitor of gastrointestinal lipase, and at least one compound selected from the group of psyllium husk, its derivatives, and salts thereof. The gastrointestinal lipase inhibitor is present in this composition in an amount at least sufficient to reduce the absorption of fat in the meal consumed by a patient. In general, this amount is preferably from about 10 mg to about 500 mg. The psyllium husk compound is preferably present in the unit dosage form in an amount of from about 500 mg to about 20 g.

A preferred method of treating or preventing the syndrome of anal leakage of oil occasionally occurring after the oral administration of a lipase inhibitor, comprises orally administering a lipase inhibitor, preferably orlistat or Pluronic L101, and psyllium husk in a dosage amount from 10 to 200 mg of lipase inhibitor and from 0.5 to 10 g of psyllium husk per fat containing meal. Most conveniently, this method comprises orally administering to a patient a composition in unit dosage form containing orlistat or Pluronic L101 and psyllium husk. The dosage amount of the composition is from 10 to 120 mg of orlistat or Pluronic L101 and from 2 to 6 g of psyllium husk, particularly about 60 mg of orlistat or Pluronic L101 and about 2.5 g of psyllium husk per fat containing meal consumed by the patient. Preferably, the composition is orally administered to the patient at breakfast, lunch and dinner.

EXAMPLE 1

Granules or pellets for the simultaneous, separate or chronologically spaced administration of orlistat or Pluronic L101 and psyllium husk are prepared as follows:

45 g of psyllium husk and 45 g of AVICEL RC-591 (microcrystalline cellulose) are mixed and kneaded with demineralized water to a suitable consistency. 10 g of psyllium husk are added and mixed in. The wet mass is sieved and then dried in a fluidized bed to give granules. Alternatively the wet mass is extruded and spheronized and then dried in a fluidized bed to give pellets. A quantity of 5 g or 10 g of granules or pellets is filled into sachets as unit dose. Alternatively, this material is filled into appropriate containers. The dosing may be performed with appropriate spoons.

EXAMPLE 2

| Powder for reconstitution: | |
| --- | --- |
| Orlistat or Pluronic L101 | 0.12 g |
| Psyllium husk | 5 g |
| Sorbitol | 7.11 g |
| AVICEL CL 611 | 1.20 g |
| .beta.-carotene | 0.06 g |
| Citric acid | 0.10 g |
| p-Hydroxybenzoic acid methyl ester | 0.15 g |
| p-Hydroxybenzoic acid propyl ester | 0.03 g |
| Flavoring agent (passion fruit) | 0.13 g |
| AVICEL PH 105 | 8.00 g |
| Monosodium citrate | 1.00 g |
| Saccharine-sodium salt | 0.10 g |
| Total | 23 g |

An oral suspension is obtained by adding tap-water to the above powder to a volume of about 100 ml.

EXAMPLE 3

| Granulates or pellets: | |
| --- | --- |
| Orlistat or Pluronic L101 | 0.120 g |
| Psyllium husk | 5.0 g |
| AVICEL PH 101 | 4.88 g |

The above ingredients are mixed and kneaded with demineralized water to obtain a suitable consistency. The wet mass is sieved and dried in a fluidized bed at a temperature below 35 degrees C. to give granules. Alternatively, the wet mass is extruded and spheronized and then dried in a fluidized bed to give pellets. A quantity of 10 g of the granules or pellets is filled into sachets as a unit dose. Alternatively, the material is filled into appropriate containers. The dosing can be performed with appropriate spoons.

EXAMPLE 4

| Effervescent tablets: | |
| --- | --- |
| Orlistat or Pluronic L101 | 0.120 g |
| Saccharose powder | 1.669 g |
| Psyllium husk | 2.5 g |
| Sodium cyclamate | 0.115 g |
| Saccharine sodium salt | 0.004 g |
| Sodium bicarbonate | 0.7 g |
| Tartaric acid (crystallized) | 1.12 g |
| Sodium chloride (milled) | 0.04 g |
| Chinine sulfate | 0.007 g |
| Flavoring agent | 0.025 g |
| Total | 6.3 g |

Orlistat or Pluronic L101, saccharose, psyllium husk, sodium cyclamate and saccharin sodium are mixed and sieved. The mixture is kneaded with a mixture of ethanol and demineralized water, granulated and dried at a temperature below 35 degree. C. in a fluidized bed to give a mixture A. Sodium bicarbonate, tartaric acid, sodium chloride, chinine sulfate and the flavoring agent are mixed and sieved to give a mixture B. A and B are mixed and compressed to effervescent tablets of 6.3 g and a diameter of 30 mm.

EXAMPLE 5

| Chewable tablets: | |
| --- | --- |
| Orlistat | 0.060 g |
| Psyllium husk | 2.5 g |
| Sorbitol | 1.84 g |
| AVICEL CE-15 | 1.0 g |
| Talc | 0.480 g |
| Sodium stearyl fumarate | 0.120 g |
| Total | 6.0 g |

Orlistat or Pluronic L101, psyllium husk, sorbitol and AVICEL CE-15 are mixed and sieved. Talc and sodium stearyl fumarate are sieved and mixed with the first obtained mixture and then the mixture is compressed to chewable tablets of 6.0 g and a diameter of 2 cm.

EXAMPLE 6

Psyllium wafers for the simultaneous, separate or chronologically spaced administration of orlistat are prepared as follows:

Corn flour (5 g) and 5 g of psyllium are mixed. Soybean oil (2 g) is added and the mixture is mixed for 15 minutes. Water is added to form a wet mass which is then extruded. The wet wafers are dried in an oven at 35. degree. C. and then packaged.

EXAMPLE 7

| Wafers: | |
| --- | --- |
| Psyllium husk | 5 g |
| Soybean oil | 2 g |
| Corn flour | 5 g |
| Orlistat or Pluronic L101 | 120 mg |

The process is the same as in Example 6 but orlistat or Pluronic L101 is first dissolved in soybean oil and added to the blend. After the wet massing with water and extrusion, the wafers are dried at 35 degree C.

EXAMPLE 8

Wafers: the proportions of the ingredients and the procedure are the same as in Example 7, but molten tripalmitin is substituted for soybean oil.

EXAMPLE 9

Psyllium wafers for the simultaneous, separate or chronologically spaced administration of orlistat are prepared as follows:

Psyllium husks (5 g) and 5 g of maltodextrin are mixed. Molten tripalmitin (2 g) is added to the mixture. The mass is then wetted with water and the wet mass is extruded. The wafers are dried at 35 degree C.

EXAMPLE 10

| Wafers: | |
|---|---|
| Psyllium husks | 5 g |
| Maltodextrin | 5 g |
| Triplamitin | 2 g |
| Orlistat or Pluronic L101 | 120 mg |

The process is the same as in Example 9 but orlistat or Pluronic L101 is dissolved in molten tripalmitin and then added to the blend. The wafers are dried at 35 degree C.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

What is claimed is:

1. A pharmaceutical composition in oral dosage form for humans, said composition comprising an inhibitor of gastrointestinal lipase, said gastrointestinal lipase is present in an amount of from about 10 mg to about 500 mg, and a compound comprising psyllium husk, seeds or leaves thereof, said compound is present in an amount of from about 500 mg to about 20 g, wherein said composition contains 10 to 50 parts by weight of the compound per 1 part by weight of the inhibitor of gastrointestinal lipase.

2. The composition according to claim 1, wherein the compound is present in an amount of from about 2 g to about 10 g and the inhibitor gastrointestinal lipase is present in an amount of from about 10 mg to about 500 mg.

3. The composition according to claim 1, wherein the inhibitor of gastrointestinal lipase is orlistat or a poloxamer.

4. The composition according to claim 1, wherein the compound is psyllium husk.

5. The composition according to claim 1, wherein the oral dosage form is selected from the group consisting of tablets, capsules, lozenges, liquid formulations, wafers and crackers.

6. The composition according to claim 1, wherein the compound is psyllium husk and the inhibitor of gastrointestinal lipase is orlistat or a poloxamer, said psyllium husk being present in the composition in an amount of from about 0.5 g to about 5 g and said orlistat or a poloxamer being present in the composition in an amount of from about 01 mg to about 120 mg.

7. The composition according to claim 6, wherein said unit dosage form is a tablet.

8. The composition according to claim 7, wherein the tablet contains about 2.5 g of psyllium husk and about 60 mg of orlistat or a poloxamer.

9. The composition according to claim 2, wherein the unit dosage form is a wafer containing from about 1 g to about 10 g of psyllium husk and from about 10 mg to about 200 mg of orlistat or a poloxamer.

10. The composition according to claim 9, wherein the wafer contains about 5 g of psyllium husk about 120 mg of orlistat or a poloxamer.

11. The composition according to claim 1, wherein the composition contains at least one auxiliary excipient.

12. A method of treating or preventing the syndrome of anal leakage of oil in a patient to whom a composition containing an inhibitor of gastrointestinal lipase is being orally administered in unit dosage form, comprising orally administering to a patient per meal consumed by the patient a composition in unit dosage form containing an inhibitor of gastrointestinal lipase present in an amount at least sufficient to reduce absorption of fat in a meal consumed by the patient, said inhibitor of gastrointestinal lipase being present in an amount of from about 10 mg to about 500 mg, and at least one compound selected from the group consisting of psyllium husk, seeds and leaves thereof, said compound being present in the unit dosage form in an amount of from about 500 mg to about 20 g.

13. A pharmaceutical composition in unit dosage form for the prevention of anal leakage of oil in a patient, said composition comprising a pharmaceutically effective amount of an inhibitor of gastrointestinal lipase, and a pharmaceutically effective amount of a compound comprising psyllium husk or any component of psyllium.

* * * * *